United States Patent
Lovell et al.

(10) Patent No.: US 9,068,902 B2
(45) Date of Patent: Jun. 30, 2015

(54) METHODS AND APPARATUS FOR EVALUATING VIBRATION RESISTANCE OF A COMPONENT OF A FLUID CONTROL VALVE

(75) Inventors: Michel Ken Lovell, Marshalltown, IA (US); Kenneth W. Junk, Marshalltown, IA (US)

(73) Assignee: FISHER CONTROLS INTERNATIONAL LLC, Marshalltown, IA (US)

( * ) Notice: Subject to any disclaimer, the term of this patent is extended or adjusted under 35 U.S.C. 154(b) by 448 days.

(21) Appl. No.: 13/468,772

(22) Filed: May 10, 2012

(65) Prior Publication Data

US 2012/0285549 A1 Nov. 15, 2012

Related U.S. Application Data

(60) Provisional application No. 61/486,016, filed on May 13, 2011.

(51) Int. Cl.
| | | |
|---|---|---|
| *G01M 7/08* | (2006.01) | |
| *F16K 37/00* | (2006.01) | |
| *G01N 29/12* | (2006.01) | |
| *G01N 29/44* | (2006.01) | |

(52) U.S. Cl.
CPC ............ *G01M 7/08* (2013.01); *F16K 37/0083* (2013.01); *G01N 29/12* (2013.01); *G01N 29/4427* (2013.01); *G01N 2291/2698* (2013.01)

(58) Field of Classification Search
CPC .... G01M 7/08; G01N 29/045; F16K 37/0083
USPC .......................................... 73/579, 168, 12.01
See application file for complete search history.

(56) References Cited

U.S. PATENT DOCUMENTS

| | | | | |
|---|---|---|---|---|
| 4,342,229 | A * | 8/1982 | Massa | 73/579 |
| 7,290,450 | B2 * | 11/2007 | Brown et al. | 73/579 |
| 7,549,336 | B2 * | 6/2009 | Masyada | 73/579 |
| 2005/0072234 | A1 * | 4/2005 | Zhu et al. | 73/579 |
| 2011/0030806 | A1 | 2/2011 | Catron | |

OTHER PUBLICATIONS

Good Year, "TensionRite Belt Frequency Meter," User Manual, May 2008, 31 pages.
Dynatension, "DynaTension Meter Model P1000," Operating Instructions, retrieved from http://www.viten-dynatension.com/p1000_manual%20.pdf, May 13, 2013, 50 pages.

* cited by examiner

*Primary Examiner* — John Chapman, Jr.
(74) *Attorney, Agent, or Firm* — Hanley, Flight & Zimmerman, LLC (57) ABSTRACT

Methods and apparatus for evaluating vibration resistance of a component of a fluid control valve are disclosed herein. An example method disclosed herein includes selecting a component of a fluid control valve and positioning a sensor relative to the selected component. The method also includes mechanically exciting the selected component, determining a resonant frequency of the selected component, and taking corrective action based on the resonant frequency of the selected component.

22 Claims, 5 Drawing Sheets

METHODS AND APPARATUS FOR EVALUATING VIBRATION RESISTANCE OF A COMPONENT OF A FLUID CONTROL VALVE

CROSS REFERENCE TO RELATED APPLICATION

This patent claims the benefit of U.S. Provisional Patent Application Ser. No. 61/486,016, filed on May 13, 2011, entitled METHODS FOR EVALUATING VIBRATION RESISTANCE OF A COMPONENT OF A FLUID CONTROL VALVE, which is incorporated herein by reference in its entirety.

FIELD OF THE DISCLOSURE

The present disclosure relates generally to fluid control valves and, more particularly, to methods and apparatus for evaluating vibration resistance of a component of a fluid control valve.

BACKGROUND

Control valves are commonly used in process control systems to control the flow of process fluids. A control valve typically includes an actuator assembly (e.g., a pneumatic actuator, a hydraulic actuator, etc.) that automates operation of the control valve. A typical actuator assembly includes an actuator having a housing that is coupled to an exterior surface of the valve body via, for example, a yoke. In addition, a control sub-assembly that automates the control valve is coupled (e.g., rigidly coupled) to the housing of the actuator. For example, the control sub-assembly may include components or instruments such as, for example, a positioner, a volume booster, a trip valve, a dump valve, etc. that are coupled (e.g., fluidly coupled) via tubing (e.g., thin-walled metal tubing).

During operation, the actuator assembly is subjected to a wide spectrum of vibration levels produced by the process system. For example, fluid flowing through a pipeline of the process system and/or process system components (e.g., pumps) may impart different frequencies of vibration to the actuator assembly. Further, the components and/or tubing of the actuator assembly may experience an amplified or increased range of vibration levels if a vibration imparted to an actuator assembly has a frequency that is similar or equal to the resonant frequency of the actuator assembly. However, the instrument tubing is often custom fit during assembly (e.g., at the factory) and is typically not tested or evaluated to determine if the tubing can withstand anticipated vibration levels and/or frequencies.

SUMMARY

An example method disclosed herein includes selecting a component of a fluid control valve and positioning a sensor relative to the selected component. The method also includes mechanically exciting the selected component, determining a resonant frequency of the selected component, and taking corrective action based on the resonant frequency of the selected component.

An example method disclosed herein includes selecting a tubing run, exciting the selected tubing run, monitoring a time-varying movement of the selected tubing run when excited, and measuring an amplitude of the time-varying movement of the selected tubing run.

An example apparatus includes a sensor to measure a time-varying movement to be positioned adjacent a selected component of the control valve assembly. A vibration exciter provides a frequency of vibration the selected component. A processor receives signals provided by the sensor and converts the signals to an output to determine the resonant frequency of the selected component.

DETAILED DESCRIPTION

In general, the example methods described herein enable evaluation of vibration resistance of a component coupled to a structure or fluid control valve. In particular, the example methods described herein provide a test to verify that a natural or resonant frequency characteristic of a component coupled to a structure is different and/or greater than a range of vibrations or frequencies of the structure during operation. For example, the example methods described herein may be used to verify that a component and/or instrument tubing custom fit to a control valve has a resonant frequency that is different than and/or greater than a range or spectrum of anticipated vibrational frequencies that will be imparted to, or produced by, the actuator assembly during operation of the actuator assembly.

The example methods described herein provide a resonant frequency test to evaluate or determine whether custom fit instrument tubing has a resonant frequency characteristic that is different than and/or greater than a resonant frequency characteristic of an actuator, a pipeline, or any other process system component that induces a vibration to the fluid control valve. Performance of a resonant frequency test may be conducted at the factory after assembly and/or in the field to predict with greater reliability or accuracy the operational life of the custom fit instrument tubing based on the anticipated levels of vibration that the component and/or the instrument tubing will experience during operation. Additionally, an instrument tubing length or run may be optimized using the example resonant frequency test or methods described herein.

Some example methods described herein enable a comparison between a resonant frequency characteristic of a component and/or instrument tubing and a recommended threshold value. For example, the recommended threshold value is different than and/or greater than an anticipated vibration frequency that may be imparted to the actuator. In some examples, the recommended threshold value may be a tenfold ratio relative to a maximum anticipated vibration level. In this manner, it can be determined with greater accuracy or confidence that the custom fit instrument tubing of a component coupled to the actuator can withstand vibrations imparted by an actuator that is vibrating, for example, at the natural or resonant frequency of the tubing.

In other examples, the methods described herein enable evaluation or verification of any other component coupled to, for example, an actuator housing such as, for example, brackets, supports, pipe nipples, fittings, and/or other hardware.

In addition to determining the resonant frequency of a component of a valve assembly, the example methods and apparatus described herein may also be used to determine or estimate a damping characteristic (e.g., a damping ratio or coefficient) of a component (e.g., a tubing run) coupled to a valve assembly. For example, a damping ratio of a system may be estimated via, for example, time-domain techniques, frequency-domain techniques and/or other suitable techniques used to determine a damping ratio of a system. The damping characteristic(s) may be used, for example, to improve or optimize the life cycle of various components coupled to a fluid valve assembly to meet a desired life cycle, reliability requirement, and/or maintenance cycle.

Figure 1:
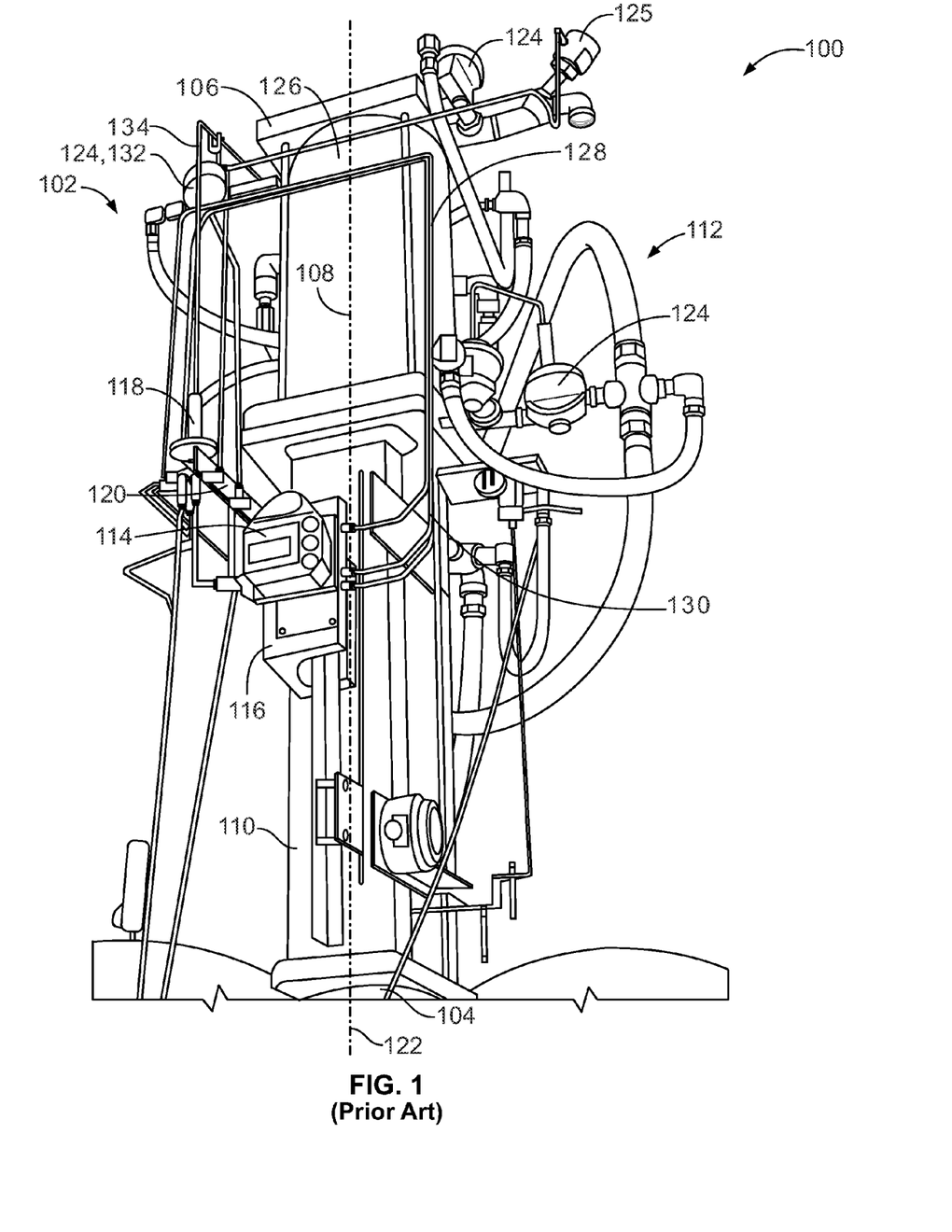
FIG. 1 illustrates a known fluid control valve.

FIG. 1 illustrates a known fluid control valve assembly 100. As shown, the fluid control valve assembly 100 includes an actuator assembly 102 coupled to a fluid valve 104. An inlet of the fluid valve 104 is to be fluidly coupled to an upstream fluid conduit (e.g., a pipeline) and an outlet of the fluid valve 104 is to be fluidly coupled to a downstream fluid conduit (e.g., a pipeline). A process fluid (e.g., water, steam, ammonia, etc.) flows between the inlet and the outlet and may induce vibrations to a pipeline of a process system and/or the actuator control valve assembly 100.

The actuator assembly 102 (e.g., a pneumatic actuator, a hydraulic actuator, etc.) automates operation of the control valve assembly 100. The actuator assembly 102 includes a cylinder or actuator 106 having a housing 108 that is coupled to the valve body 104 via a yoke 110. In the illustrated example, the actuator 106 is cantilevered from, or substantially perpendicular to, the fluid flow path through the fluid valve 104.

In addition, the actuator assembly 102 of the illustrated example includes a sub-assembly or components 112 to automate the control valve assembly 100. Such components 112 are coupled (e.g., rigidly coupled) to the housing 108 and/or the yoke 110. In the illustrated example, a controller or positioner 114 is mounted to the yoke 110 via a mounting bracket 116 and a trip valve 118 is mounted to the yoke 110 via a mounting bracket 120 extending substantially perpendicular relative to a longitudinal axis 122 of the actuator 106. The trip valve 118 causes the actuator assembly 102 to move to a fail-safe position (e.g., a fail-up position, a lock-up position, a fail-down position) when a pressure of a supply or control fluid (e.g., air, hydraulic oil, etc.) of the actuator 106 falls below a predetermined value. To increase the stroking speed of the actuator 106, the control valve assembly 100 of FIG. 1 includes one or more volume boosters 124 coupled to pipe components such as pipe nipples, tees and crosses. The actuator assembly 102 may also include one or more dump valves 125 and/or any other fluid control devices that enable automation of the actuator assembly 102.

To fluidly couple the components 112, the example actuator assembly 100 of FIG. 1 employs instrument tubing 126. In particular, the instrument tubing 126 is a rigid metal tubing (e.g., stainless steel tubing) and typically has a diameter of approximately three-eighths of an inch (⅜"). However, in other examples, the diameter of the instrument tubing 126 may be between, for example, a quarter inch (¼") and one and one-quarter inch (1¼").

For example, the positioner 114 is fluidly coupled to the trip valve 118 via instrument tubing runs 128 and 130. As shown, a span of the instrument tubing runs 128 and 130 is a considerable distance, which results in a relatively low tubing rigidity. Also, the trip valve 118 is coupled to a valve booster 132 via an instrument tubing run 134, which also spans a considerable distance.

During assembly or manufacture of the control valve assembly 100, the instrument tubing 126 is custom fit to the control valve assembly 100. Due to the customization of the control valve assembly 100, an instrument tubing run, configuration or layout (e.g., tubing runs 128, 130 or 134) may vary between a first control valve assembly and a second control valve assembly. In addition, the custom fit tubing run(s) may not be configured to have an optimized resonant frequency characteristic.

The control valve assembly 100 is configured to withstand anticipated vibration levels that may be imparted to the control valve assembly 100 by, for example, pipeline vibration caused by fluid flowing through a process system during operation. In some applications, the actuator 106 may become very excited and significantly amplify a pipeline vibration when the pipeline vibration produces a frequency similar to the resonant frequency of the actuator 106. At the resonant frequency, the actuator 106 tends to oscillate at a relatively large (e.g., maximum) amplitude, thereby imparting elevated and/or abnormally high levels of vibration to, for example, the components 112 and/or the instrument tubing 126. Thus, in addition to the vibrations produced by a process system, the components 112 and/or the instrument tubing 126 may be subjected to elevated levels of vibration of the actuator assembly 102.

If the instrument tubing 126 is assembled to the actuator 106 such that an instrument tubing run (e.g., any of the instrument tubing runs 128, 130 and 134) has a resonant frequency characteristic that is within a range (e.g., similar to) the frequency levels produced by a process system and/or the actuator assembly 102, the instrument tubing 126 may vibrate at its resonant frequency at elevated acceleration levels. A resonant vibration at elevated levels may cause the instrument tubing 126 to vibrate or oscillate in a violent manner, causing the instrument tubing 126 to break, fracture, fatigue and/or otherwise become damaged. Thus, an instrument tubing run having a relatively low resonant frequency characteristic is more likely to become damaged when exposed to a range of vibration frequencies typically found in an operating process system, whereas an instrument tubing run having a relatively high resonant frequency characteristic (i.e., a resonant frequency greater than the range of frequencies typically found in operation of a process system) is not likely to become damaged due to vibration.

In addition, the resonant frequency of the actuator assembly 102 may vary between different control valves. For example, long-stroke actuators (e.g., a stroke length greater than 10 inches) have an increased weight (e.g., mass) and dimensional envelope compared to, for example, a short-stroke actuator (e.g., a stroke length less than 10 inches). Thus, a long-stroke actuator composed of the same material as a short-stroke actuator may have a less structural stiffness than a short-stroke actuator. As a result, a long-stroke actuator typically exhibits a resonant frequency that is significantly lower than the resonant frequency of a short-stroke actuator. In practice, the lower resonant frequency of long-stroke actuators typically amplifies the relatively low frequency pipeline vibrations of a process system. Therefore, the components 112 and the instrument tubing runs (128, 130 and 134) of the actuator assembly 102 may be subjected to a significant or wide spectrum of vibration frequencies at a wide range of amplitudes.

In addition, customizing the instrument tubing runs 128, 130 and/or 134 to each particular control valve makes it difficult to ensure that the resonant frequency of the instrument tubing is different than and/or greater than the excitation frequencies imparted by a process system and/or the actuator assembly 102. As a result, such instrument tubing customization may provide an instrument tubing run that may not reliably withstand the anticipated vibration of the process system or the elevated vibrations of an actuator.

Figure 2:
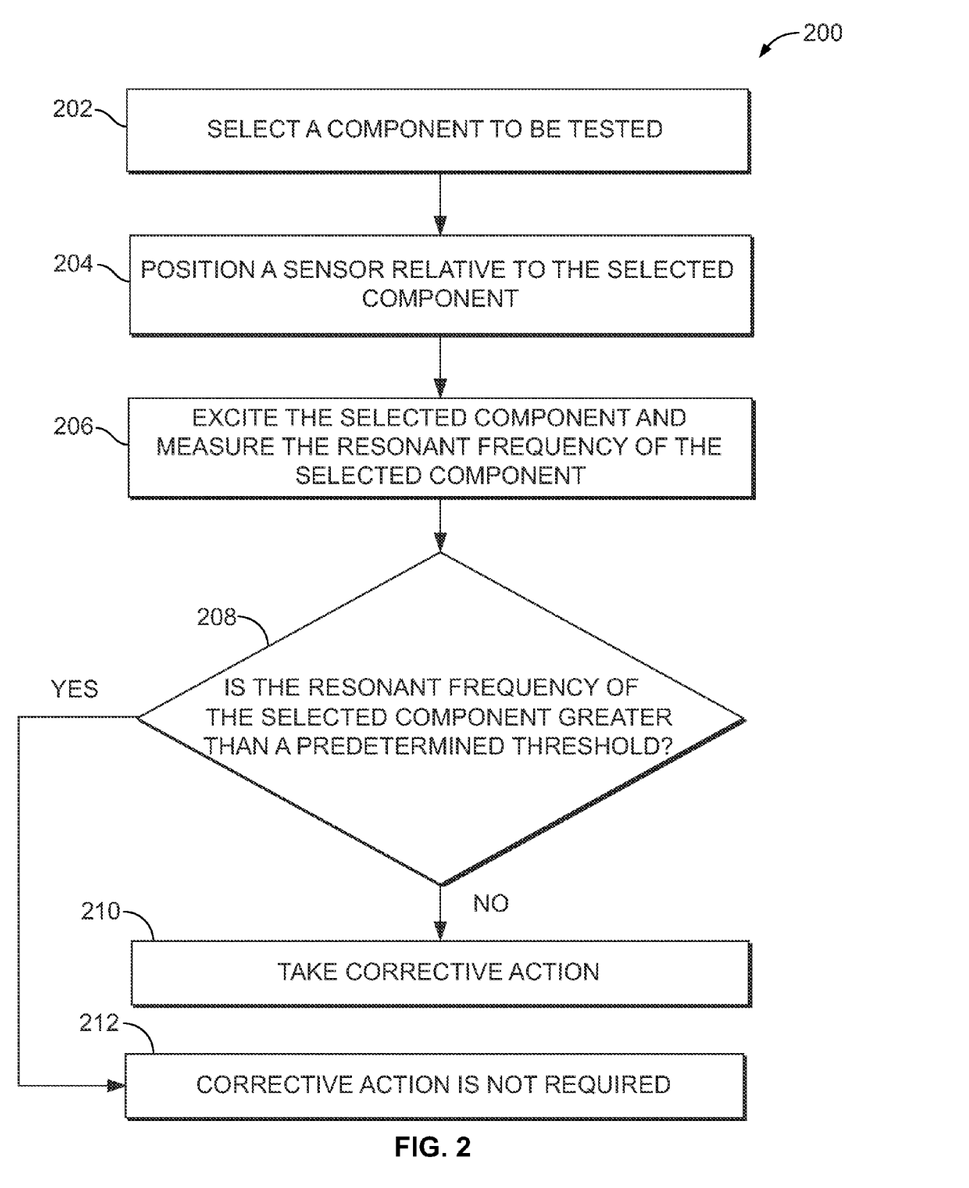
FIG. 2 is flowchart illustrating an example method described herein to evaluate vibration resistance of a component of a fluid control valve.

FIG. 2 is an example flowchart illustrating an example method 200 to verify or evaluate a vibration resistance of a component of a control valve assembly such as, for example, the control valve assembly 100 of FIG. 1. The example method 200 of FIG. 2 is particularly advantageous for determining a resonant frequency of an instrument tubing run that is custom fit to a control valve.

After assembly of a fluid control valve assembly, a component of the fluid control valve assembly for which determination of a resonant frequency is desired is selected (block 202). A component of a fluid control valve assembly may include an instrument tubing length or run that spans between fittings or instruments. For example, the instrument tubing run 128 of FIG. 1 that spans between the positioner 114 and the trip valve 118 may be a selected for evaluation.

Although the example method 200 of FIG. 2 is described in connection with an instrument tubing run, the example method 200 of FIG. 2 may also be applied to any other component (e.g., the components 112), mounting bracket, fitting, and/or any other control device of an actuator assembly.

After the component or instrument tubing run to be tested is selected at block 202, a sensor is then positioned on or adjacent a portion of the instrument tubing run (block 204). In some examples, the sensor may be positioned relative to an approximate midpoint of the tubing run and/or positioned relative to any other portion or the selected tubing run. In other examples, although the position of the sensor relative to the tubing run is not a sensitive variable to measuring the resulting frequency of the tubing, the sensor may be positioned relative to a portion of the selected component or instrument tubing run that has a least amount of stiffness as described below.

For example, the sensor may be an accelerometer, an optical sensor (e.g., an infrared sensor, an LED sensor), a piezo type sensor, an acoustic sensor, or any other sensor that may be used to detect or measure frequency. For example, if the sensor is an optical sensor, the sensor may be positioned at a distance between approximately three-eighths of an inch (3/8") and two inches (2") from the selected instrument tubing run determined at block 202. The sensor may be held manually by an operator relative to the selected tubing run or may be mounted relative to the selected tubing run via a mounting bracket or other fixture device. For example, if the sensor is an accelerometer, then the accelerometer may be attached directly to the portion of the selected instrument tubing run determined at block 204. If the sensor is an acoustic sensor, a microphone may be directly coupled or clipped to the selected tubing run. Alternatively, a first microphone may be coupled to a first fitting coupled to a first end of the tubing run and a second microphone may be coupled to a second fitting coupled to a second end of the tubing run.

After the sensor is positioned at block 204, the selected tubing run is then excited via, for example, a vibration exciter (block 206). For example, the selected tubing run may be excited manually via a vibration exciter (e.g., a rubber hammer), a force transducer or any other suitable impact device or method to excite the structural resonance of the instrument tubing run and provide a stable frequency of vibration to the selected tubing run. The sensor provides a signal to, for example, a measuring device (e.g., a computer, a microprocessor, a hand held metering device, etc.), which in turn provides or converts the signal provided by the sensor into an output reading, for example, of oscillations per second (e.g., a unit of hertz). This process can be repeated to verify repeatability of the measured value.

If the output value provided by the measuring device is less than a predetermined threshold (block 208), then corrective action to the selected instrument tubing is required (block 210). If the output value provided by the measuring device is greater than a predetermined threshold (block 208), then corrective action to the selected instrument tubing (which is custom fit to the control valve) is not required (block 212).

The predetermined threshold value may be greater than, for example, a known maximum resonant frequency of a pipeline, a range of vibration frequencies produced by a control valve assembly (e.g., the actuator assembly 102 of FIG. 1) and/or a known range of vibration frequencies that may be produced (i.e., amplified or elevated) by an actuator assembly oscillating at its resonant frequency. For example, the predetermined threshold value may be a resonant frequency that is greater than, for example, a minimum threshold of 60 hertz, 200 hertz, etc., for an instrument tubing having a diameter of approximately (3/8"). For example, the predetermined threshold value may be determined based on a safety ratio that may be a tenfold value relative to the maximum frequency that would be produced by anticipated vibrations of a process system or an actuator assembly.

If the measured resonant frequency of the selected instrument tubing is less than predetermined threshold at block 208, then corrective action to the selected instrument tubing is required because the selected instrument tubing may have a resonant frequency that falls within a range of vibration frequencies that may be imparted to a process system (e.g., the pipeline) or which may be amplified or elevated by an actuator assembly. In other words, an instrument tubing run having resonant frequency below the minimum threshold will resonate when the process system or an actuator assembly produces vibrations having a frequency substantially equal to the resonant frequency of the instrument tubing. As a result, the instrument tubing may fatigue, flex, bend or otherwise become damaged during operation. As described below, corrective action may include re-bending or re-shaping the instrument tubing, providing tubing supports, etc. As noted above, the example method 200 of FIG. 2 may be conducted in the factory or the in the field.

Further, to help identify in taking corrective action, identification of the least stiff portion (and its direction) may be helpful in taking corrective action. For example, identifying a portion of the tubing run having the least amount of stiffness is helpful in taking corrective action by, for example, bending the tubing differently along the portion having the least stiffness and/or supporting the portion of the tubing run having the least amount of stiffness via a brace, bracket, a tie, etc. An example method that may be employed to locate or detect which portion of the selected tubing run has the least amount of stiffness includes manually flexing the selected instrument tubing run in each direction of a degree of freedom in which the component or the tubing run may flex or bent. The portion of the selected tubing run that deflects or bends the most for a given load relative to other portions of the selected instrument tubing typically has the least amount of stiffness. For example, a midpoint of an instrument tubing run or length that is unsupported typically has the least amount of stiffness.

Although not shown, the measuring device may include a processor to receive the signal provided by the sensor. Additionally, the measuring device may include a comparator to compare the output reading based on the signals received by the sensor with a predetermined threshold value (e.g., from a look-up table, in memory, etc.) and provide a warning (e.g., an audible warning) to an operator inspecting the selected instrument tubing when the resonant frequency of the selected instrument tubing run is below the predetermined threshold. After corrective action is taken, the corrected instrument tubing may be retested via the example method 200 of FIG. 2.

Figure 3:
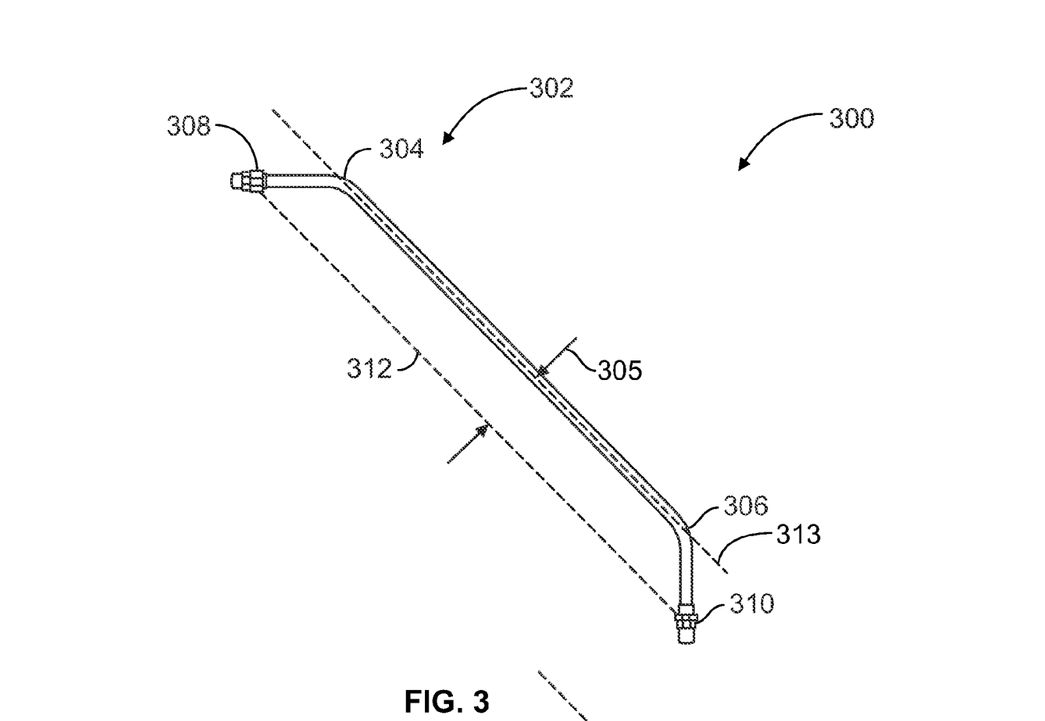
FIG. 3 depicts an example instrument tubing run having a relatively high resonant frequency.

FIG. 3 illustrates an example instrument tubing run 300 that has a relatively high resonant frequency. For example, the instrument tubing run 300 illustrates an optimized tubing run or length based on a corrective action prompted by the example method 200 of FIG. 2. Although mounting locations of components or instruments (e.g., the components 112 of FIG. 1) determine the length or span of the tubing run, tubing bend locations 302 may have a significant impact on the resonant frequency of the tubing run 300. Thus, a corrective action may include removing a tubing run having a relatively low resonant frequency (e.g., the tubing run 128 of FIG. 1), straightening a tubing run to substantially remove any bends, and re-bending the tubing at locations that provide a relatively higher resonant frequency or optimized tubing length or run. For example, closely coupling the tubing relative to a fitting axis 312 defined by the fittings 308 and 310 may provide a relatively higher resonant frequency. For example, as shown in FIG. 3, the illustrated tubing run 300 includes two bends 304 and 306 (e.g., approximately 45 degree bends) adjacent respective fittings 308 and 310 to form a tubing axis 313 substantially parallel to fitting axis 312 having a separation distance 305. In general, a decreased separation distance 305 may provide a mechanically stiffer tubing run 300 resulting in a relatively higher resonant frequency. Alternatively, corrective action may include positioning components or instruments that are coupled by the instrument tubing relatively closer to each other. For example, the positioner 114 of FIG. 1 may be positioned closer to the trip valve 118 such that the instrument tubing run 128 or 130 may span a shorter distance. Any other suitable corrective action may include using instrument tubing having a increased diameter, tubing having larger wall thickness, employing mounting brackets to secure or support the instrument tubing to the actuator 106, etc.

Figure 4:
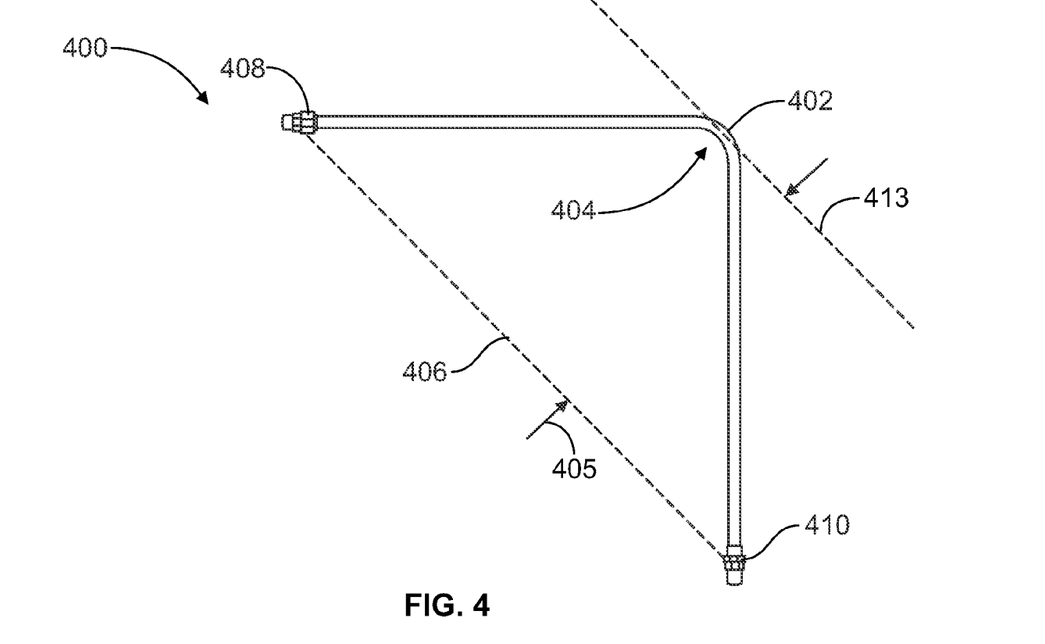
FIG. 4 depicts an example instrument tubing run having a relatively low resonant frequency.

FIG. 4 illustrates an example instrument tubing run 400 that has a relatively low resonant frequency. As shown in FIG. 4, the tubing run 400 includes a single bend 402 approximately 90 degrees, resulting in a midpoint 404 of the tubing run 400 being located at a significant distance from a line 406 between fittings 408 and 410. The increased separation distance 405, defined by an axis 413 formed parallel to the line 406 between fittings 408 and 410 and intersecting the midpoint 404 of the tubing run 400, is much greater than decreased separation distance 305 of FIG. 3. The increased separation distance 405 thereby exhibits a lower resonant frequency.

Figure 5:
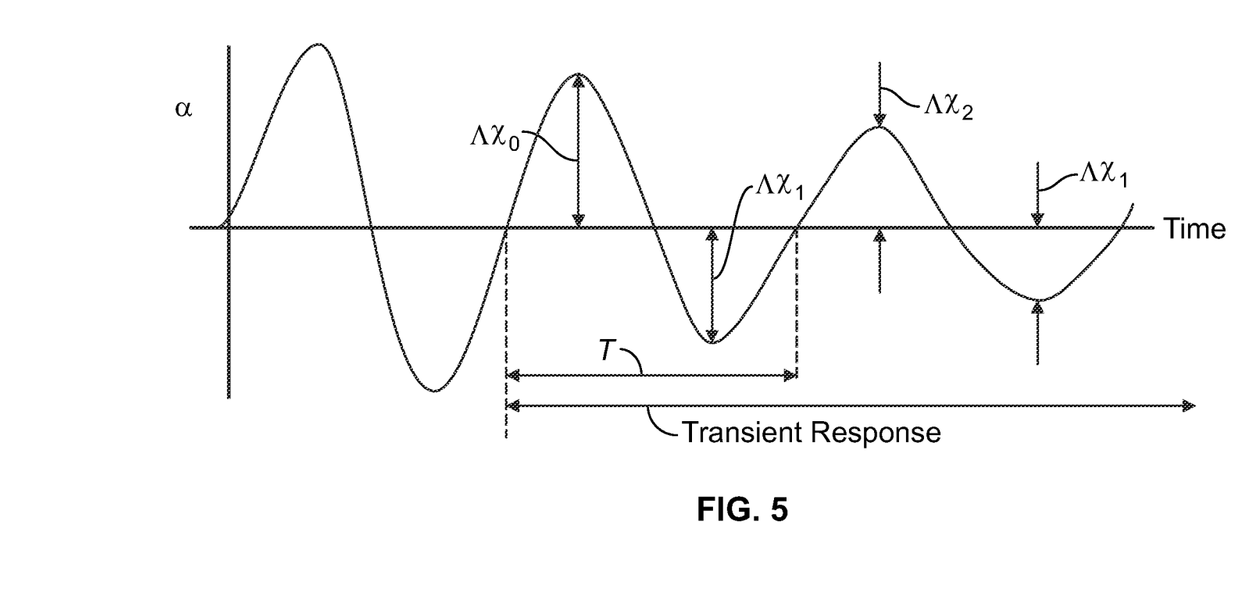
FIG. 5 depicts an example graph illustrating amplitude decay over a period of time.

In addition to determining the resonant frequency of a component of a valve assembly, the example methods and apparatus described herein may also be used to determine or estimate a damping characteristic (e.g., a damping ratio or coefficient) of a component (e.g., a tubing run) coupled to a valve assembly (e.g., the control valve assembly 100 of FIG. 1). For example, the sensing device or sensor from which vibration frequency information is obtained may also be used to obtain amplitude decay characteristics. In particular, when testing a component such as a tubing run (e.g., any of the tubing runs 128, 130 or 134 of FIG. 1), a mechanical excitation (e.g., an impact) may be imparted to the tubing run to vibrate the tubing run. The sensor may be used to monitor the displacement of the tubing and, thus, can be used to track or record the time-varying movement of the tubing. The tubing will tend to move or displace at its resonant frequency. Additionally, the amplitude will also tend to decay or decrease over time in a manner consistent with the damping characteristics of the tubing. For example, FIG. 5 depicts an example graph illustrating amplitude decay over a period of time.

Once obtained, the decay characteristic(s) of the vibration amplitude of the tubing can be used to estimate or determine a damping characteristic such as a damping ratio. Any known method of calculating the damping characteristic may be used including, for example, the logarithmic decrement method and/or the fractional overshoot method. Once the damping characteristic is determined, a transfer function may be determined and/or a finite element analysis (FEA) may be performed to estimate a performance characteristic of the tubing. For example, a fatigue FEA may be used to predict the life cycle of the tubing in anticipated use conditions. More generally, the damping characteristic(s) may be used to improve or optimize the life cycle of various components coupled to a fluid valve assembly to meet a desired life cycle, reliability requirement, and/or maintenance cycle.

Figure 6:
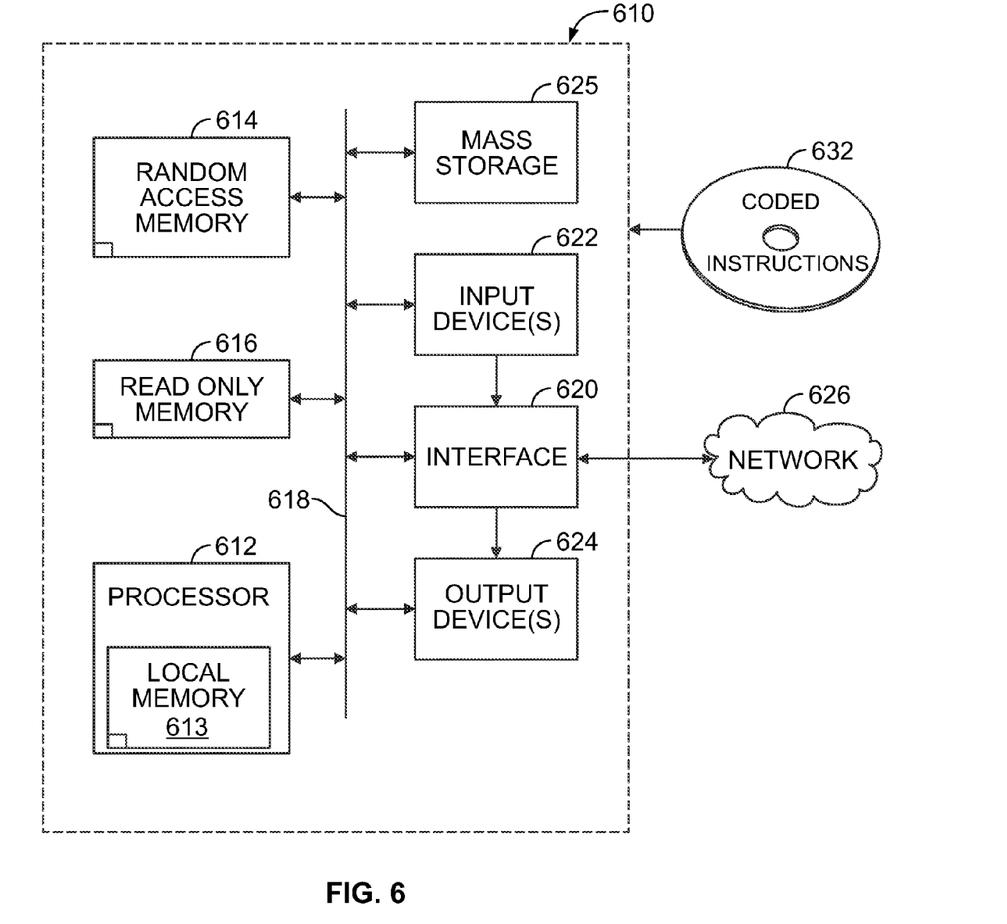
FIG. 6 is a block diagram of an example processor system that may be used to implement the example methods and apparatus described herein.

FIG. 6 is a block diagram of an example processor system 610 capable of executing or processing the signals from the sensors and/or measuring device in blocks 206 and 208 of FIG. 2.

The processor system 610 of the instant example includes a processor 612. The processor 612 may be any suitable processor, processing unit or microprocessor. Although not shown in FIG. 6, the processor system 610 may be a multi-processor system and, thus, may include one or more additional processors that are identical or similar to the processor 612 and that are communicatively coupled to a bus 618. For example, the processor 612 can be implemented by one or more microprocessors or controllers from any desired family or manufacturer.

The processor 612 includes a local memory 613 (e.g., a cache) and is in communication with a main memory including a volatile memory 614 and a non-volatile memory 616 via the bus 618. The volatile memory 614 may be implemented by Synchronous Dynamic Random Access Memory (SDRAM), Dynamic Random Access Memory (DRAM), RAMBUS Dynamic Random Access Memory (RDRAM) and/or any other type of random access memory device. The non-volatile memory 616 may be implemented by flash memory and/or any other desired type of memory device.

The processor system 610 also includes an interface circuit 620. The interface circuit 620 may be implemented by any type of interface standard, such as an Ethernet interface, a universal serial bus (USB), and/or a PCI express interface.

One or more input devices 622 are connected to the interface circuit 620. The input device(s) 622 permit a user to enter data and commands into the processor 612. The input device(s) can be implemented by, for example, a keyboard, a mouse, a touchscreen and/or a voice recognition system.

One or more output devices 624 are also connected to the interface circuit 620. The output devices 624 can be implemented, for example, by display devices (e.g., a liquid crystal display, a cathode ray tube display (CRT), a printer and/or speakers). The interface circuit 620, thus, typically includes a graphics driver card.

The interface circuit 620 also includes a communication device such as a modem or network interface card to facilitate exchange of data with external computers via a network 626 (e.g., an Ethernet connection, a digital subscriber line (DSL), a telephone line, coaxial cable, a cellular telephone system, etc.) to enable the processor system 610 to communicate with another processor system.

The processor system 600 also includes one or more mass storage devices 628 for storing software and data. Examples of such mass storage devices 628 include floppy disk drives, hard drive disks, compact disk drives and digital versatile disk (DVD) drives.

Coded instructions of the measuring device and/or processor may be stored in the mass storage device 625, in the volatile memory 614, in the non-volatile memory 616, and/or on a removable storage medium such as a CD or DVD 632.

Although certain example methods and apparatus have been described herein, the scope of coverage of this patent is not limited thereto. On the contrary, this patent covers all methods, apparatus, and articles of manufacture fairly falling within the scope of the appended claims either literally or under the doctrine of equivalents.

What is claimed is:

1. A method comprising:
   selecting a component of a fluid control valve;
   positioning a sensor relative to the selected component;
   mechanically exciting the selected component;
   determining a resonant frequency of the selected component; comparing the resonant frequency of the selected component to a predetermined resonant frequency of the fluid control valve; and
   reconfiguring the selected component to have a relatively higher resonant frequency when the resonant frequency of the selected component is within a threshold of the predetermined resonant frequency of the fluid control valve.

2. A method of claim 1, further comprising processing signals provided by the sensor to determine the resonant frequency of the selected component in units of hertz.

3. A method of claim 2, further comprising using an actuator of the fluid control valve to determine the predetermined resonant frequency, wherein the predetermined resonant frequency corresponds to vibrations induced by or imparted to the actuator of the fluid control valve.

4. A method of claim 1, wherein mechanically exciting the selected component comprises impacting the selected component.

5. A method of claim 1, wherein the selected component comprises a tubing run.

6. A method of claim 1, further comprising identifying a portion of the selected component having a least amount of stiffness when taking corrective action.

7. A method of claim 6, wherein identifying the portion of the selected component having the least amount of stiffness comprises manually deflecting the selected component.

8. A method of claim 1, wherein positioning the sensor relative to the selected component comprises positioning the sensor at approximately a midpoint of a tubing length or span.

9. A method of claim 1, further comprising processing sensor signals to determine a damping ratio of the selected component.

10. A method of claim 1, further comprising using the damping ratio to predict a life cycle of the selected component.

11. A method of claim 9, wherein processing the signals comprises using a logarithmic decrement method or a fractional overshoot method.

12. A method of claim 1, wherein selecting the component comprises selecting at least one of a tubing run, a mounting bracket, or a fitting of the control valve.

13. A method comprising:
    selecting a component of a fluid control valve, wherein the selected component includes a tubing run;
    positioning a sensor relative to the selected component;
    mechanically exciting the selected component;
    determining a resonant frequency of the selected component;
    taking corrective action based on the resonant frequency of the selected component by reconfiguring the selected component to have a relatively higher resonant frequency by bending the tubing to have at least two bends.

14. A method comprising:
    selecting a tubing run coupled to an actuator assembly of a fluid control valve;
    exciting the selected tubing run;
    monitoring a time-varying movement of the selected tubing run when excited;
    measuring an amplitude of the time-varying movement of the selected tubing run;
    determining a resonant frequency based on the amplitude of the time-varying movement of the selected tubing run;
    comparing the resonant frequency of the time-varying movement to a predetermined resonant frequency of the actuator assembly; and
    adjusting the selected tubing run by bending a portion of the selected tubing run when the resonant frequency of the time-varying movement is within a threshold of the predetermined resonant frequency of the actuator assembly.

15. A method of claim 14, wherein monitoring the time-varying movement of the selected tubing run comprises receiving a signal from a sensor positioned adjacent the selected tubing run.

16. A method of claim 14, wherein monitoring the time-varying movement of the selected tubing run comprises positioning a first sensor adjacent a first end of the selected tubing run and positioning a second sensor adjacent a second end of the selected tubing run.

17. A method of claim 14, further comprising identifying a portion of the selected tubing run having a least amount of stiffness.

18. A method of claim 17, wherein identifying the portion of the selected tubing run having the least amount of stiffness comprises manually flexing the selected tubing run in each direction of a degree of freedom in which the selected tubing run flexes or bends.

19. A method of claim 14, further comprising removing any bends in the selected tubing run, and re-bending the selected tubing run at locations that provide a relatively higher resonant frequency.

20. A method of claim 14, further comprising obtaining decay characteristics based on the amplitude the time-varying movement of the selected tubing run and estimating a damping ratio of the selected tubing run.

21. A method of claim 20, further comprising using a logarithmic decrement method to estimate the damping ratio.

22. A method of claim 21, further comprising conducting a fatigue finite element analysis based on the estimated damping ratio to predict a life cycle of the selected tubing run.

\* \* \* \* \*